United States Patent [19]
Ouchi

[11] Patent Number: 5,897,487
[45] Date of Patent: Apr. 27, 1999

[54] FRONT END HOOD FOR ENDOSCOPE

[75] Inventor: Teruo Ouchi, Saitama, Japan

[73] Assignee: Asahi Kogaku Kogyo Kabushiki Kaisha, Tokyo, Japan

[21] Appl. No.: 09/059,424

[22] Filed: Apr. 14, 1998

[30] Foreign Application Priority Data

Apr. 15, 1997 [JP] Japan ................................. 9-097112
May 27, 1997 [JP] Japan ................................. 9-136259

[51] Int. Cl.$^6$ ............................................. A61B 1/04
[52] U.S. Cl. .......................... 600/127; 600/129; 600/175
[58] Field of Search ................................. 600/104, 106, 600/121, 123, 125, 127, 129, 175

[56] References Cited

U.S. PATENT DOCUMENTS

| | | | |
|---|---|---|---|
| 5,448,990 | 9/1995 | De Faria-Correa | 600/129 |
| 5,662,588 | 9/1997 | Iida | 600/127 X |
| 5,667,475 | 9/1997 | Laser et al. | 600/127 |
| 5,716,321 | 2/1998 | Kerin et al. | 600/127 X |

FOREIGN PATENT DOCUMENTS

| | | |
|---|---|---|
| 8-84700 | 4/1996 | Japan . |
| 8-131397 | 5/1996 | Japan . |
| 9-66019 | 3/1997 | Japan . |

*Primary Examiner*—Beverly M. Flanagan
*Attorney, Agent, or Firm*—Greenblum & Bernstein, P.L.C.

[57] ABSTRACT

A front end hood for an endoscope allows an observation image of a portion which is transmitted through the transparent front end hood to be less distorted, and produces an excellent observation image even in a periphery of a wide visual field. An optically transparent front end hood projects from a front end insertion portion of an endoscope so that an observation port located in the front end face of the front end insertion portion is positioned inside the front end hood. A portion of the front end hood may be formed into a spherical shape, the diameter of which decreases toward the opening end of the front end hood.

22 Claims, 16 Drawing Sheets

FRONT END HOOD FOR ENDOSCOPE

BACKGROUND OF THE INVENTION

The present invention relates to a front end hood fixedly secured to or detachably attached to a front end portion of an endoscope.

The front end hood is widely used to carry out various endoscopic treatments efficiently with safety since the front end hood provided on the front end portion of an endoscope can ensure a sufficient distance between the endoscope and an object to be subjected to the required treatment. Even if the object exists in a narrow space where the endoscope cannot be separated from the object, the front end hood ensures such a distance to enable the endoscopic observation.

For example, Japanese Patent Kokai Publication No. 9-66091 discloses an endoscope equipped with a front end hood or cap 92 in combination with a high-frequency snaring treatment tool 97 as shown in FIG. 23. The mucosa of a diseased part is previously pulled into the front end hood 92 by means of suction, and the root portion of the diseased part is then tightened and snared with the high-frequency snaring treatment tool 97.

To enable the endoscopic observation in a wide visual field, the front end hood 92 is made of an optically transparent material so that the object can be observed through the front end hood 92 in the peripheral portion of the visual field.

However, the light beam from the object to be observed is inevitably passed in an inclined manner through the front end hood 92 in the peripheral portion of the visual field as shown by an arrow in FIG. 23, and therefore, the observed image of the object in the peripheral portion of the visual field is distorted.

SUMMARY OF THE INVENTION

It is an object of the invention to provide a front end hood for an endoscope, which can ensure an excellent observation image in the wide visual field.

To attain the above-noted object, a front end hood according to a first aspect of the present invention is provided with a diameter-increased portion by which an opening end of the front end hood is made larger in diameter than the opposite end thereof attachable to an insertion section front end portion of an endoscope. The provision of such diameter-increased portion can enlarge or widen a range of a visual field in which the light beam from the object can directly reach an observation port of the endoscope without being passed though the front end hood.

A front end hood according to a second aspect of the present invention is provided with a diameter-decreased portion by which the light beam from the object in the peripheral portion of the visual field can be passed through the front end hood at the right angle or an angle closer to the right angle. Due to the provision of such diameter-decreased portion, the light beam from the object in the peripheral portion of the visual field can reach an observation port of the endoscope with being passed through the front end hood at the right angle or the angle closer to the right angle, the less-distorted observation image of the object in the peripheral portion of the visual field can be obtained.

The present disclosure relates to subject matter contained in Japanese Patent Application Nos. 9-97112 (filed on Apr. 15, 1997), and 9-136259 (filed on May 27, 1997), which are expressly incorporated herein by reference in their entireties.

DETAILED DESCRIPTION OF FRONT END HOOD

Figure 1:
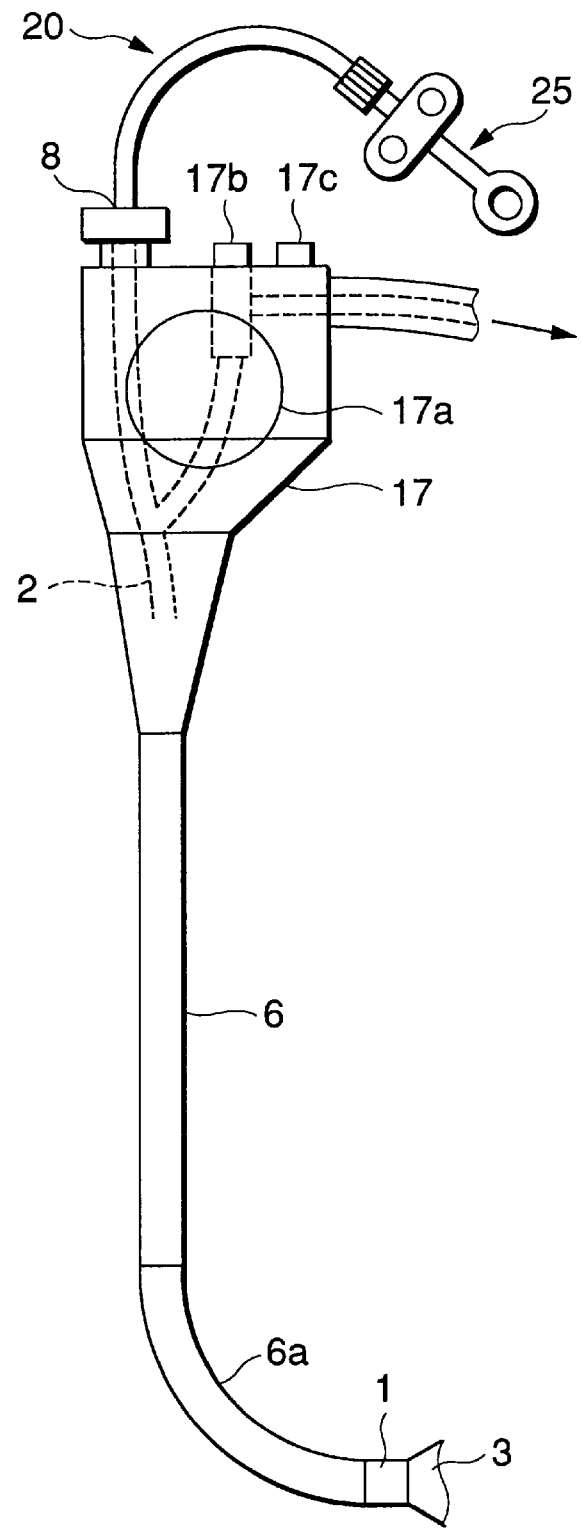
FIG. 1 is an external view showing the entire configuration of an endoscope for ligation treatment, to which a frond end hood of the present invention is provided.

FIG. 1 shows the entire configuration of an endoscope for ligation treatment. The rear end of an insertion section 6 which is formed by a flexible tube is coupled to an operating section 17. The insertion section 6 has a front end portion 1 and a curved portion 6a adjacent the front end portion 1. The curved portion 6a can be bent by remote operation through an operation knob 17a disposed on the operating section 17. The reference numeral 3 designates a front end hood which is attached to the front end portion 1 of the insertion section 6.

Figure 4:
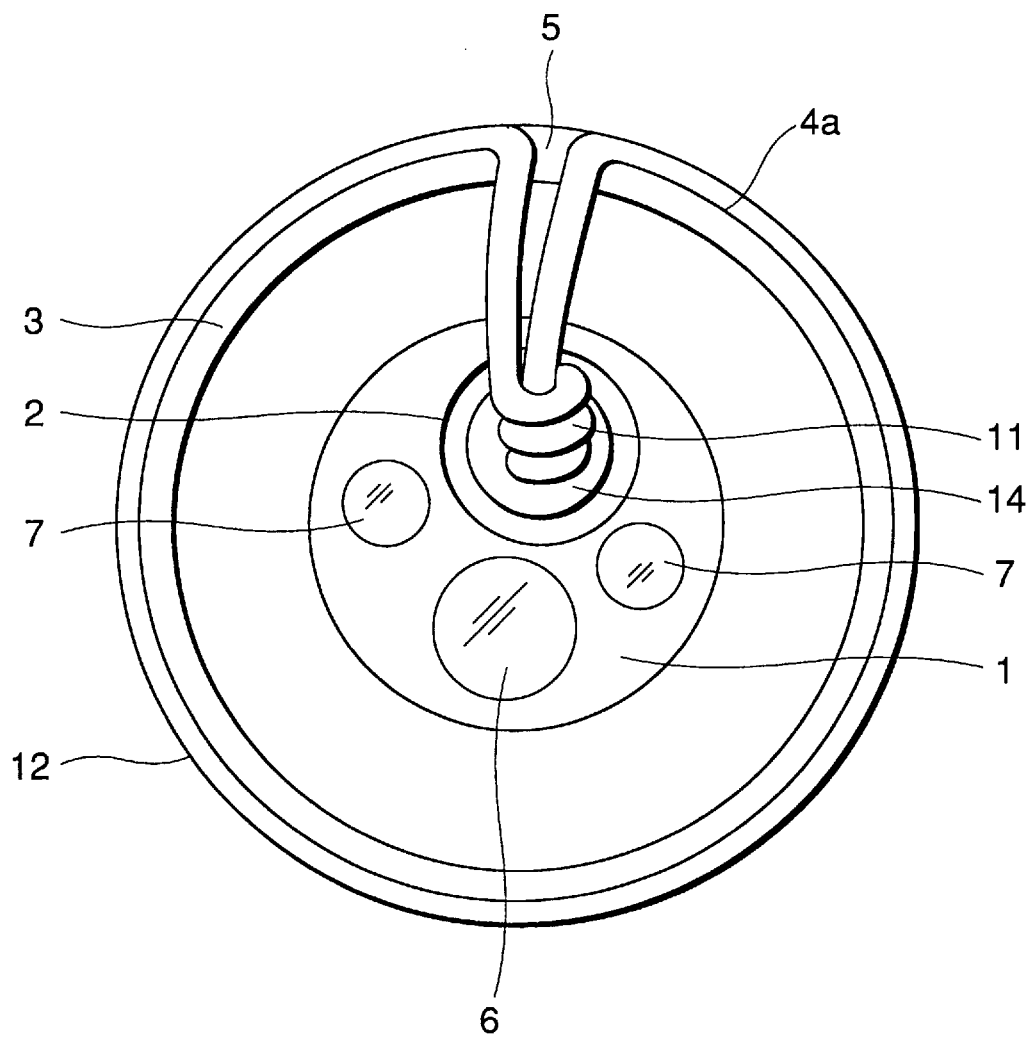
FIG. 4 is a front view showing the front end hood shown in FIG. 3.

A treatment tool insertion channel 2 is passed through the insertion section 6, and is opened at the front end face of the insertion section front end portion 1 as shown in FIG. 4. A forceps plug is attached to an insertion port 8 of the treatment tool insertion channel 2 on the operator-side end. The reference numeral 20 designates a ligation treatment tool which is inserted into and passed through the treatment tool insertion channel 2. The detail of the tool will be described later. The reference numeral 25 designates an operating section which is disposed on the operator-side end of the ligation treatment tool 20.

The reference numeral 17c designates an air and water supply button, and 17b is a suction operation button for suction operation through the treatment tool insertion channel 2, which is connected between an external suction device (not shown) and the treatment tool insertion channel 2.

As shown in FIG. 4, functional elements including (but not limited to) an observation port 6, an illumination port 7, and an outlet opening of the treatment tool insertion channel 2 are disposed in the front end face of the insertion section front end portion 1.

Figure 3:
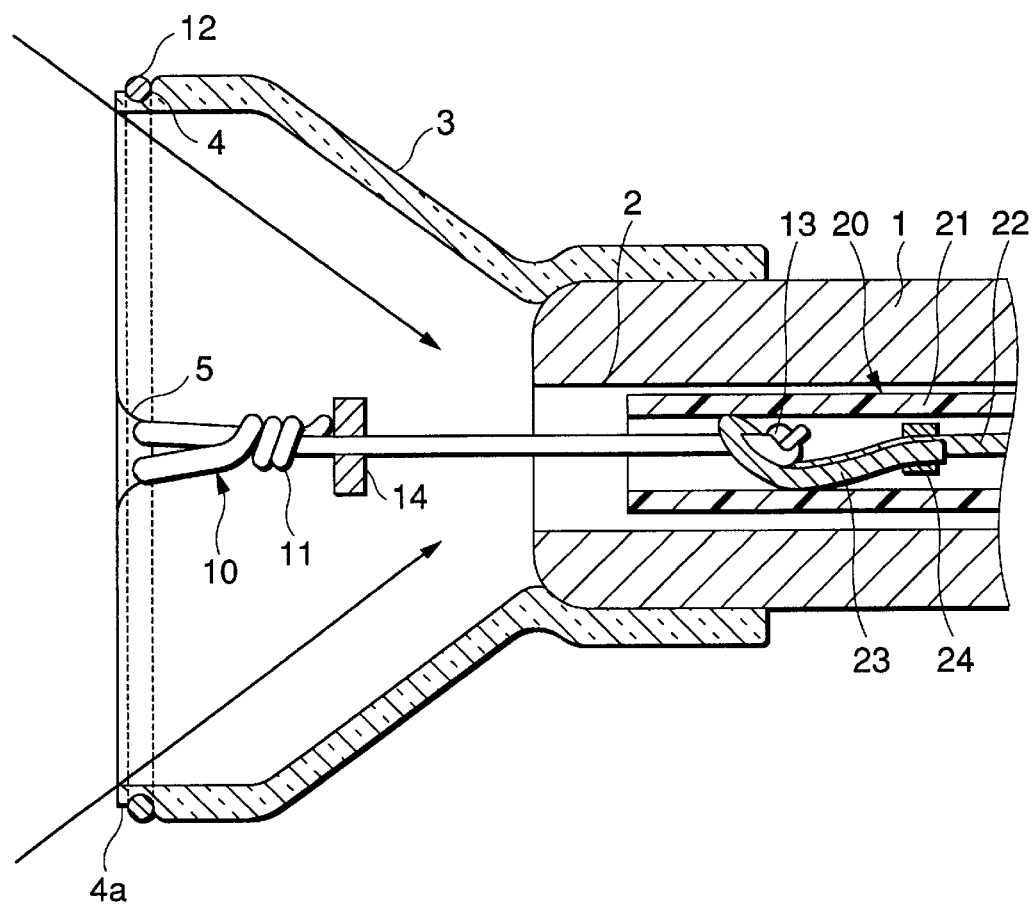
FIG. 3 is a side section view showing the front end hood attached to an insertion section front end portion of the endoscope.

FIG. 3 shows the front end hood 3 in an enlarged manner. The front end hood 3 is detachably fitted on the insertion section front end portion 1 of the endoscope so that the front end hood 3 projects forwardly from the front end face of the insertion section front end portion 1. The observation port 6, the illumination port 7, and the outlet opening of the treatment tool insertion channel 2 are positioned inside the front end hood 3. The treatment tool insertion channel 2 serves also as a suction channel.

The front end hood 3 may be made of an optically transparent material. The front end hood 3 has a trumpet-like shape (or a funnel-like shape) so that the diameter of the front opening end of the front end hood 3 is larger than the diameter of the insertion section front end 1 of the endoscope. The diameter of the front end of the hood 3 depends on the site where the endoscope is to be used. When the endoscope is to be used in the large intestine, for example, the diameter is set to be about 10 to 30 mm. When the front end hood 3 is applied to a rigid peritoneoscope, the diameter may be increased to about 50 mm.

Since the front end hood 3 has such a conical shape that the diameter thereof is gradually larger toward the front opening end thereof, the excellent observation image in the wide visual field can be obtained inside the front end hood 3. That is, the front end hood 3 is provided with a diameter-increased portion in the form of a conical shape so that an opening end of the front end hood is made larger in diameter than the opposite end thereof attached to the insertion section front end portion 1 of the endoscope. The provision of such diameter-increased portion can enlarge or widen a range of a visual field in which the light beam from the object such as a diseased part to be observed can directly reach the observation port 7 of the endoscope without being passed though the front end hood 3 as shown by an arrow in FIG. 3.

Figure 5:
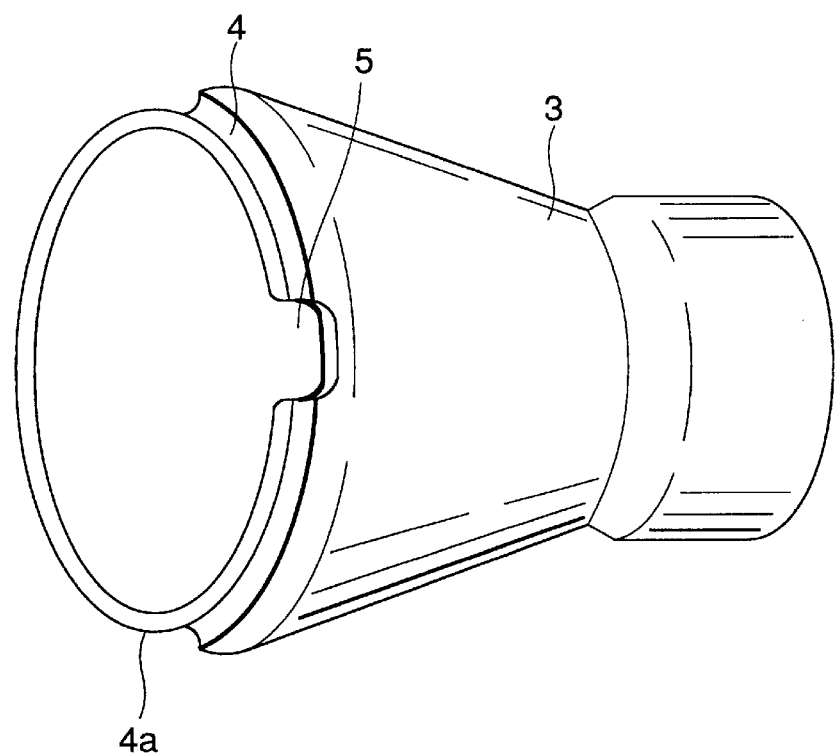
FIG. 5 is a perspective view of the front end hood shown in FIG. 3.

As best shown in FIGS. 3 and 5, an annular groove 4 is formed in the front end of the front end hood 3 to circumscribe the outer periphery thereof entirely. The annular groove 4 is adapted to receive a loop 12 of a ligature loop wire 10 which will be described later.

In order to facilitate the detachment of the loop 12 from the annular groove 4, a wall 4a defining the front end of the annular groove 4 (the left side in the FIG. 3) is made smaller in height. The reference numeral 5 designates a guide notch through which the end portion of the ligature loop wire 10 fitted into the annular groove 4 of the front end hood 3 is pulled into the inside of the front end hood 3.

Figure 6:
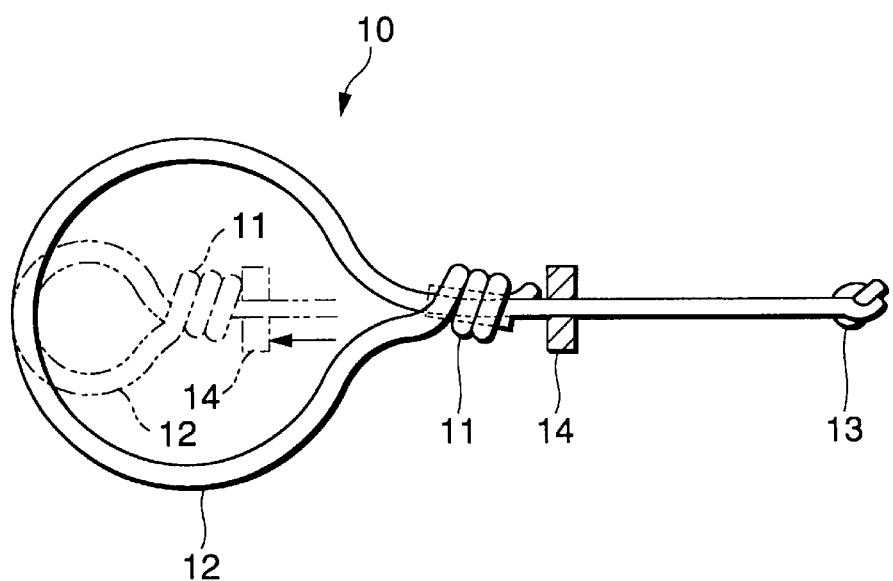
FIG. 6 is a plan view of a ligature loop wire.

FIG. 6 shows the ligature loop wire 10 in detail. The ligature loop wire 10 is made of a soft material but resistant to a tensile force, such as nylon yarn. The wire 10 may be made of another material which is selected from a wide variety of materials.

One end of the ligature loop wire 10 is wound several times so as to have a coil-like shape. A middle portion of the ligature loop wire 10 is passed through a central through hole of the coil-like-wound end 11. A lump portion 13 in the form of a knot is formed on the other end of the ligature loop wire 10.

The reference numeral 14 designates a disk-like tightening member having a through hole in a central portion thereof, through which the wire is loosely passed. The middle portion of the wire 10 is passed through both the through hole of the coil-like end 11 and the through hole of the tightening member 14.

When the lump portion 13 is fixed and the coil-like end 11 is pushed by the tightening member 14 toward the loop 12, the diameter of the loop 12 is reduced so as to perform ligation. In the case where the coil-like end 11 is thick, the tightening member 14 may be omitted and the coil-like end 11 may be directly pushed.

Returning to FIG. 3, the ligation treatment tool 20 comprises a sheath 21 formed by a flexible tube which is inserted into and passed through the treatment tool insertion channel 2, and an operating wire 22 which is passed through the sheath 21 and axially movable relative to the sheath 21.

The front end portion of the operating wire 22 is folded back and then fixed to a middle portion of the wire by a fixing tube 24, thereby forming an annular portion 23 having a size which allows the annular portion 23 to be removably retained on the lump portion 13 of the ligature loop wire 10.

Figure 2:
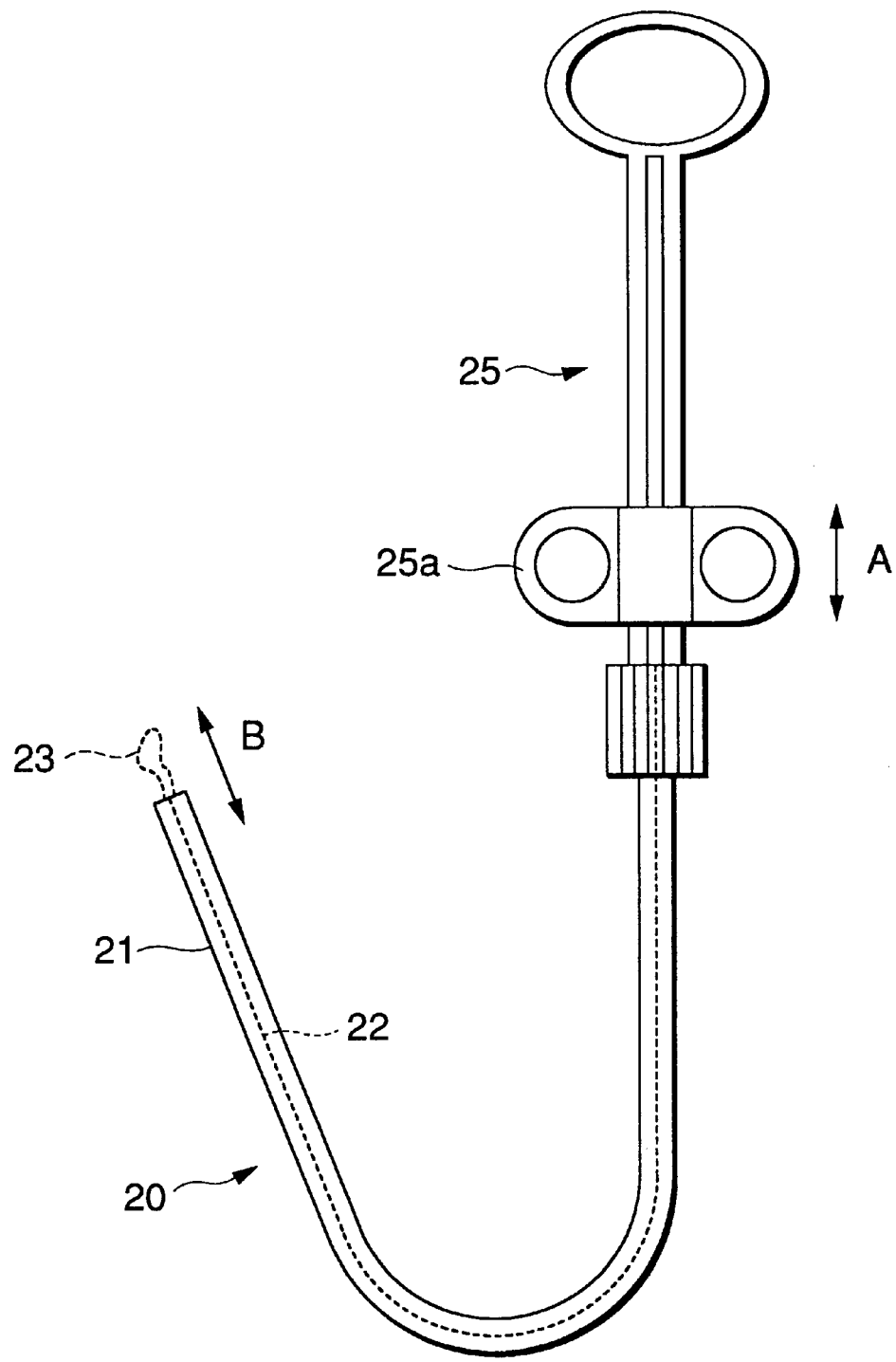
FIG. 2 is a front view of a ligation treatment tool.

FIG. 2 shows the entire configuration of the ligation treatment tool 20. The operating section 25 is coupled to the rear end of the sheath 21. When a slide handle 25a which is slidably attached to the operating section 25 is slid in the directions of the arrows A, the operating wire 22 inside the sheath 21 is moved forwardly and backwardly in the axial direction, so that the front end annular portion 23 is protruded from or retracted into the front end of the sheath 21 as indicated by the arrows B.

Figure 7:
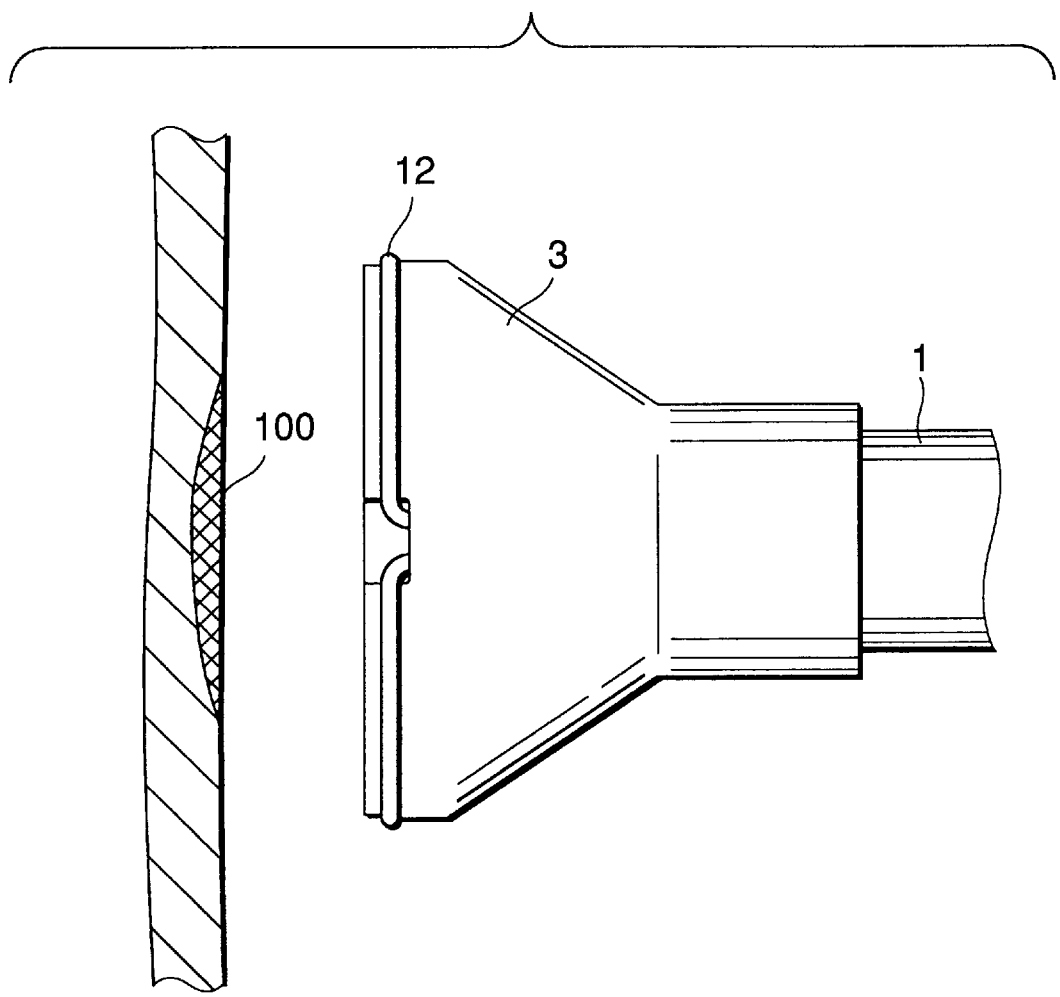
FIG. 7 is a side view of a use state of the endoscope for ligation treatment, which is provided with the front end hood shown in FIG. 3.

FIGS. 7 to 10 show an example of ligature treatment with the endoscope equipped with the front end hood 3 shown in FIG. 3. As shown in FIG. 7, first, the front opening end of the front end hood 3 is opposed to a diseased part 100 which is produced in a wide range of the mucosa surface.

Figure 8:
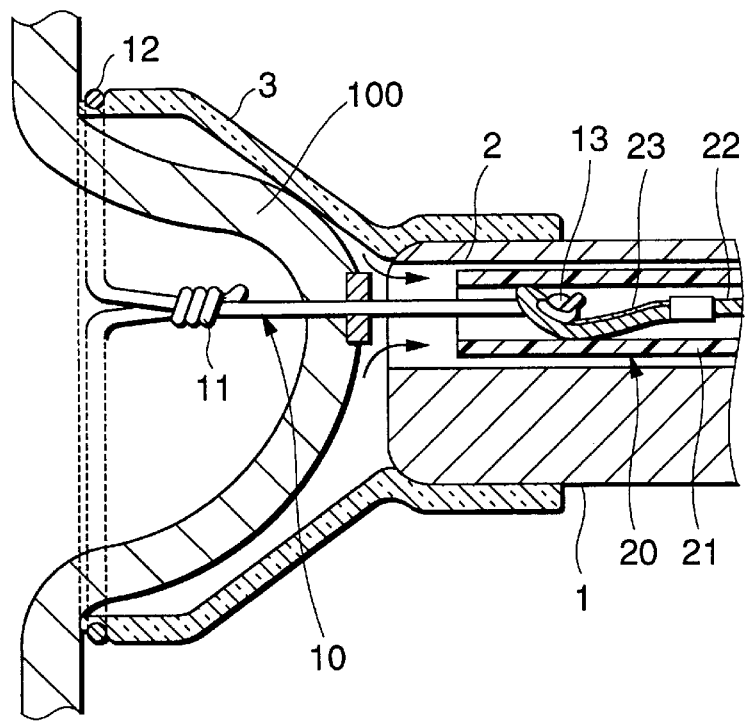
FIG. 8 is a side section view of a use state of the endoscope for ligation treatment.

As shown in FIG. 8, thereafter, the front opening end of the front end hood 3 is pressed against the mucosa surface so as to surround the diseased part 100, and the sucking is then performed through the treatment tool insertion channel 2. As a result, the diseased part 100 is sucked into the front end hood 3 and the organ wall is swollen. Since the front opening end of the front end hood 3 has a large opening area, a wide range of the organ wall can be pulled into the front end hood 3.

Figure 9:
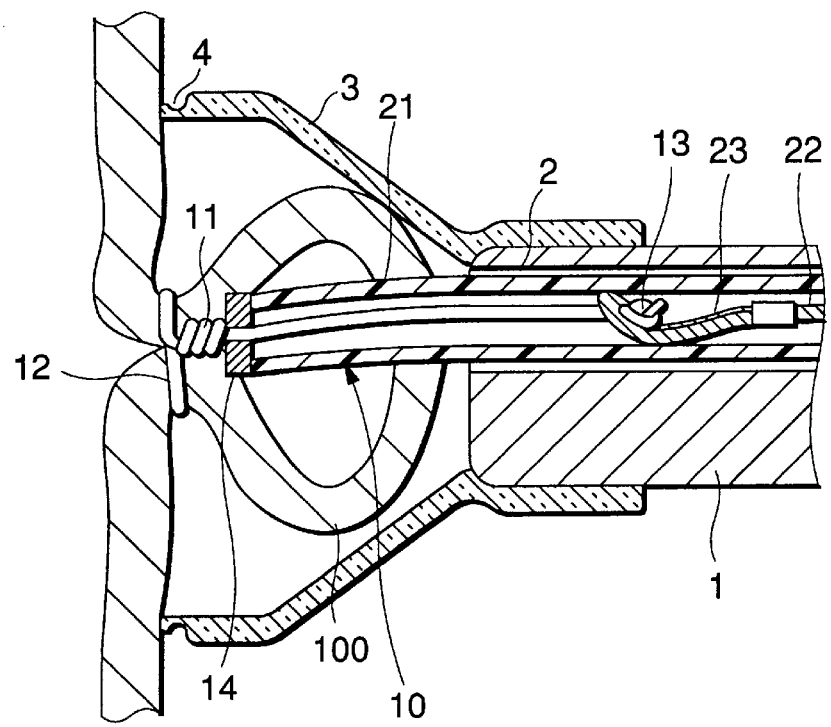
FIG. 9 is a side section view of a use state of the endoscope for ligation treatment.

Thereafter, as shown in FIG. 9, the sheath 21 is pushed forwardly to push the tightening member forwardly while pulling the operating wire 22 toward the operator-side end, so that the diameter of the loop 12 of the ligature loop wire 10 is reduced and the loop is removed from the annular groove 4 of the front end hood 3, thereby attaining a state where the root portion of the diseased part 100 is tightened.

The front end hood 3 is made of a flexible material as described above. When the diameter of the loop 12 of the ligature loop wire 10 is reduced, therefore, the front end hood 3 is deformed in the diameter-reduction direction and the loop 12 is easily removed from the annular groove 4.

Figure 10:
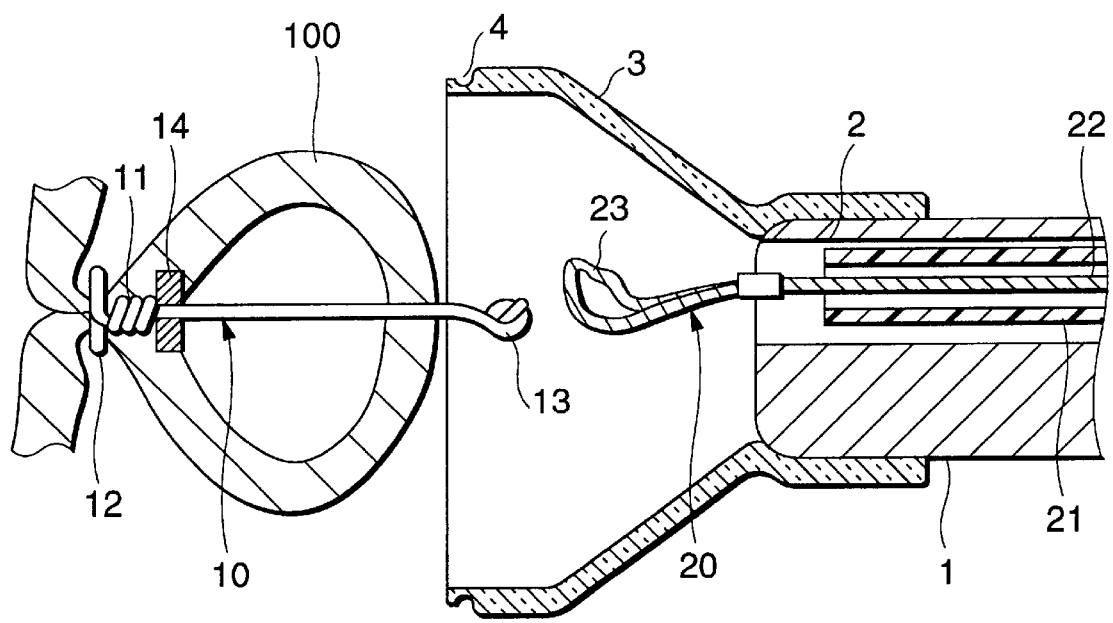
FIG. 10 is a side section view of a use state of the endoscope for ligation treatment.

After the root portion of the diseased part 100 is surely ligated by the ligature loop wire 10 as described above, the sheath 21 is pulled backward toward the operator-side end and the operating wire 22 is pushed forwardly, whereby the front end annular portion 23 of the operating wire 22 is disengaged from the lump portion 13 of the ligature loop wire 10 as shown in FIG. 10. In this way, the ligation treatment is completed.

Figure 11:
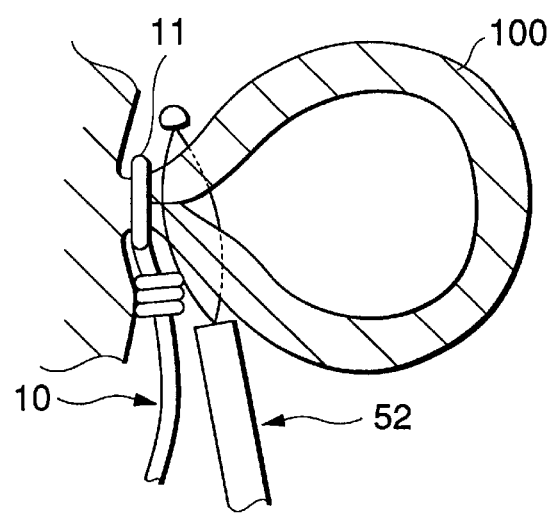
FIG. 11 is a side section view showing resection procedure after the ligation operation using the endoscope for ligation treatment is completed.
Figure 12:
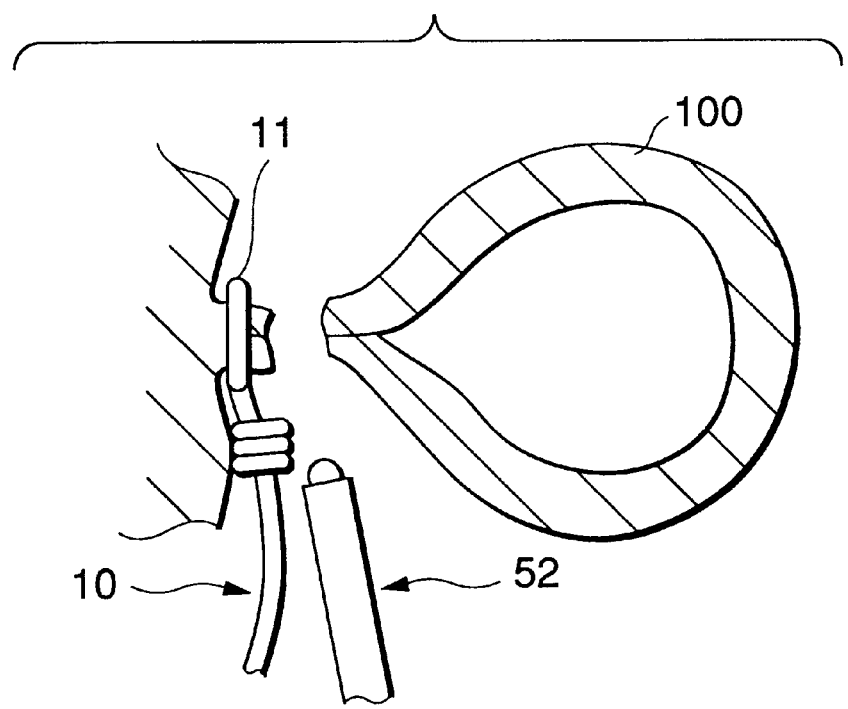
FIG. 12 is a side section view showing resection procedure after the litigation operation using the endoscope for ligation treatment is completed.

As shown in FIG. 11, thereafter, a high-frequency snare 52 is introduced through a treatment tool insertion channel of an endoscope, the projecting mucosa is tightened at a position which is closer to the diseased part 100 than the ligation site by the ligature loop wire 10, and a high-frequency current is then supplied. As a result, the diseased part 100 is resected as shown in FIG. 12.

In this way, a wide range of the organ wall can be easily tightened and resected. The use of the large front end hood 3 allows not only the mucosa but also the whole of the wall of stomach or the wall of large intestine to be ligated and resected.

Figure 13:
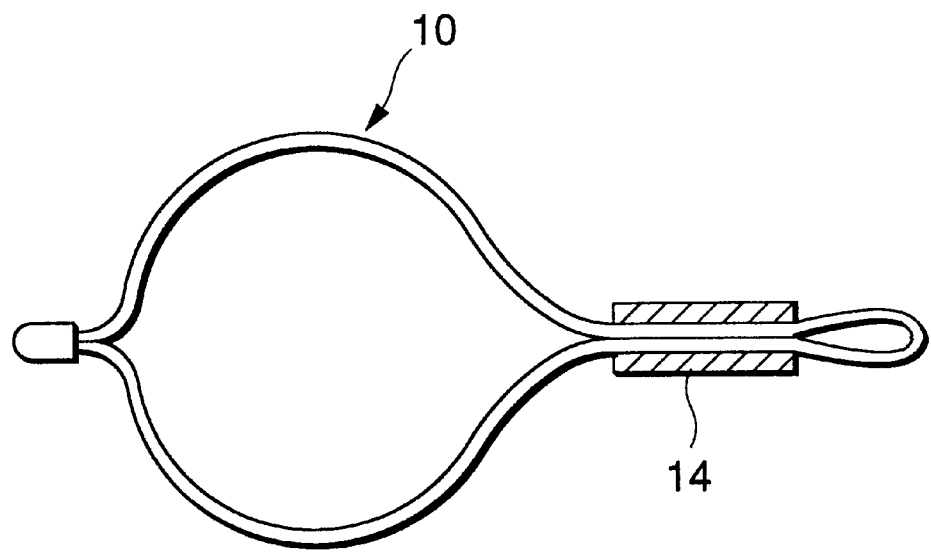
FIG. 13 is a plan section view of another ligature loop wire.

In addition, the configuration of the ligature loop wire 10 is not restricted to the aforementioned configuration, and may be realized by various kinds of structures. As shown in FIG. 13, for example, the whole of the loop wire may be formed into one loop-like shape and the diameter of the loop may be reduced by sliding the tightening member 14.

Figure 14:
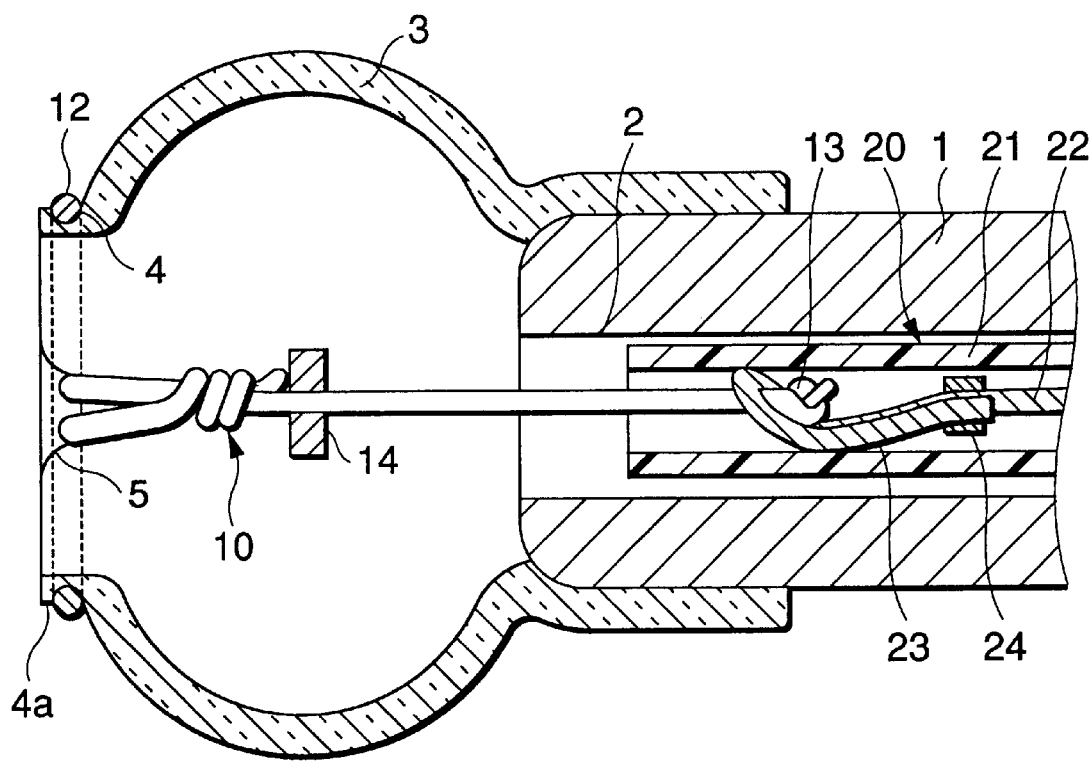
FIG. 14 is a side section view showing another front end hood attached to the insertion section front end portion of the endoscope for ligation treatment.

FIG. 14 shows another front end hood 3 attached to the front end portion 1 of an endoscope. The front end hood 3 is formed into such a bulged shape that the diameter of the middle portion is larger than that of the insertion section front end 1 and also that of the front opening end of the front end hood 3. The bulged middle portion of the front end hood 3 is spherical. The front end hood 3 is made of optically transparent material.

Figure 16:
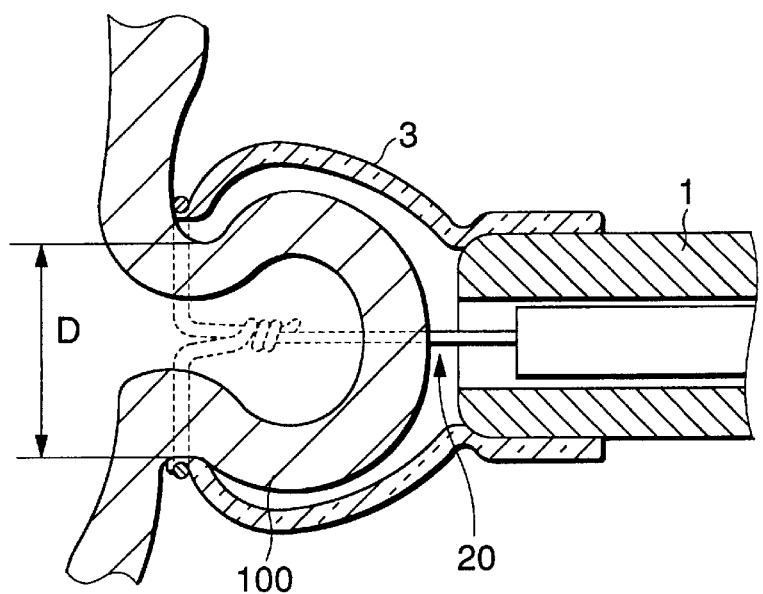
FIG. 16 is a side section view showing a state where a polyp is sucked.

When such a shape is employed, a wide range of the mucosa can be pulled into the front end hood 3 since the inside space of the front end hood 3 is enlarged. Furthermore, the ligation site positioned in the front opening end of the front end hood 3 can be made thin, and hence the ligation operation can be facilitated. That is to say, as shown in FIG. 16, since the diameter D of the stem of the sucked polyp 100 is reduced by the shape of the front end hood 3 to, for example, 60% or less of the diameter of the head portion of the polyp 100, the ligation operation for the sucked polyp 100 with the ligation tool 20 can be facilitated.

Figure 15:
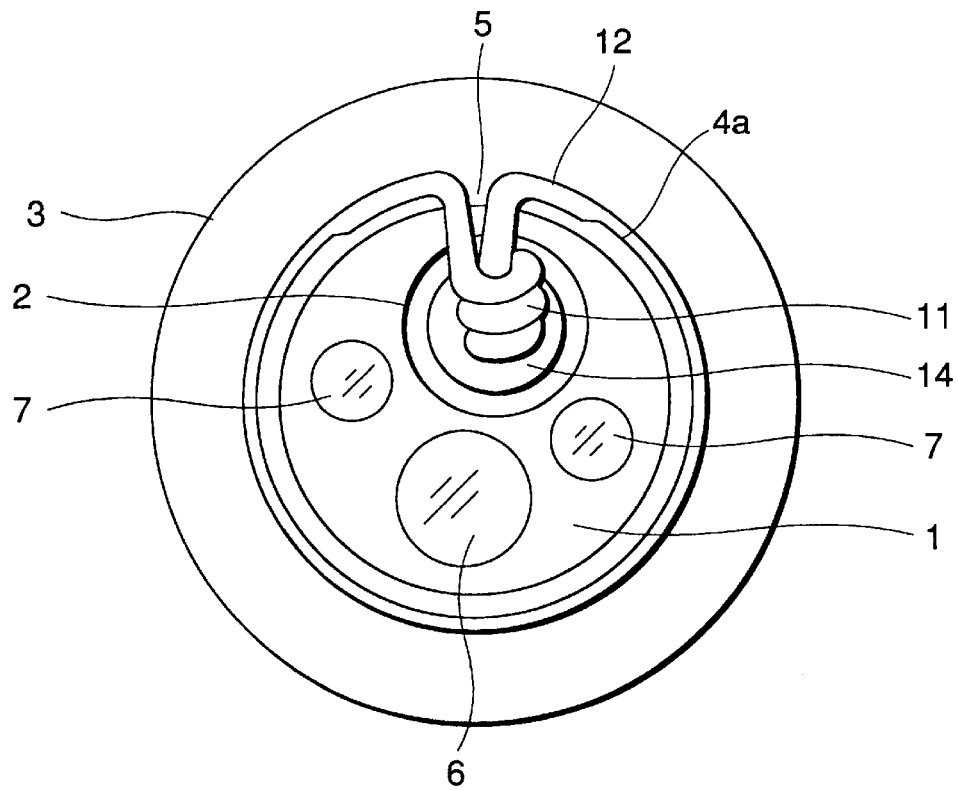
FIG. 15 is a front view of the front end hood shown in FIG. 14.

As shown in FIG. 15, the wall 4a of the annular groove 4 on the front opening end of the front end hood 3 is partly cut away by a suitable width which is larger than the guide notch 5, the removal of the loop 12 from the annular groove 4 during the ligation operation can be facilitated.

The front end hood 3 shown in FIG. 14 has a spherical, diameter-decreased portion by which the light beam from the object in the peripheral portion of the visual field can be passed through the front end hood 3 at the right angle or an angle closer to the right angle.

Figure 17:
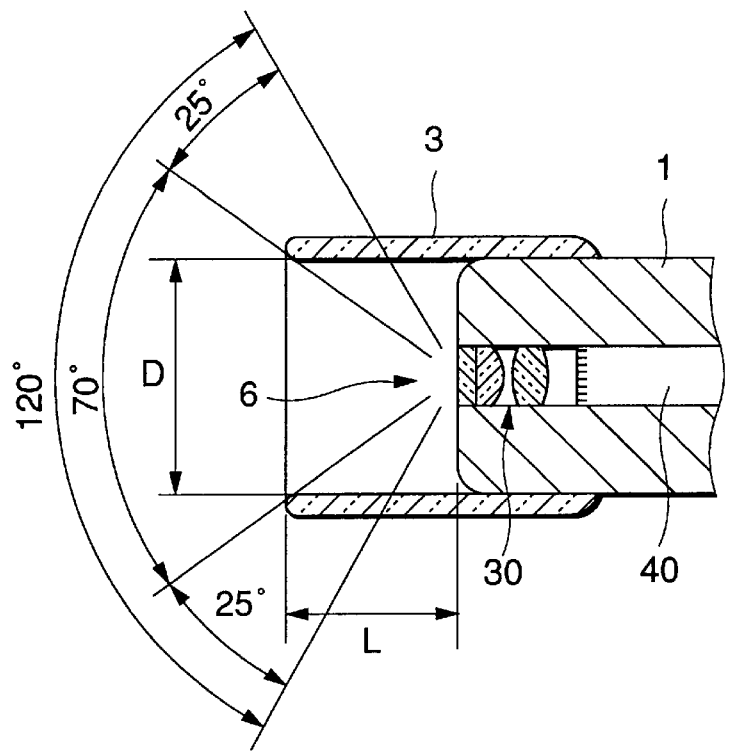
FIG. 17 is a side section view schematically showing a front end hood having a simple cylindrical shape.
Figure 18:
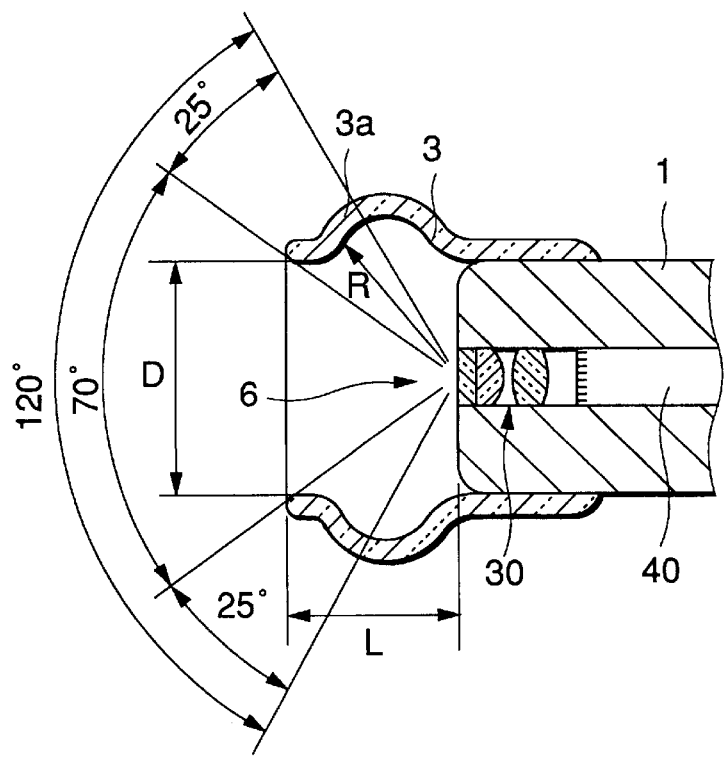
FIG. 18 is a side section view schematically showing the front end hood shown in FIG. 14.

FIG. 17 schematically shows a case where the front end hood 3 having a simple cylindrical shape is attached to the insertion section front end 1 of the endoscope, whereas FIG. 18 schematically shows a case where the frond end hood 3 shown in FIG. 14 is attached to the same insertion section front end 1. Note that the illustration for the annular groove 4 and so on is omitted in these drawings.

In these drawings, reference numeral 30 designates an objective optical system disposed inside an observation port 6. In general, the maximum visual field of the objective optical system used for the endoscope is 120° to 140°. The reference numeral 40 designates an image guide fiber. An image-incident end face of the image guide fiber 40 is placed at the image forming position of the objective optical system 30. A light receiving face of a solid-state imaging device may be placed instead of the image guide fiber 40.

For comparison, assume that the objective optical system 30 has the maximum visual field angle of 120°, the length L from the front end face of the insertion section front end portion 1 of the endoscope to the front opening end of the front end hood 3 is the same, and the diameter of the front opening end of the front hood 3 is the same in both cases. At least the portion of the front end hood 3 through which observation light beams are transmitted has a uniform thickness.

In the case shown in FIG. 17, an excellent observation image can be obtained in the central visual field range of 70° in which the observation is not conducted through the front end hood 3. In the peripheral visual field range which is outside the above-mentioned range and up to the range of 120°, however, the observation image is distorted since the observation needs to be conducted through the transparent wall of the front end hood 3 and the light beam from the object to be observed enters obliquely into the transparent wall of the front end hood 3.

In contrast, in the case shown in FIG. 18, an excellent observation image can be obtained in the central visual field range of 70°, and even in the peripheral visual field range which is outside the above-mentioned range and up to the range of 120°, the less-distorted observation image can be obtained since a diameter-reduced portion 3a of the bulged portion of the front end hood 3 allows the light beam from the object to enter into the transparent wall of the front end hood 3 substantially perpendicularly. That is to say, the front end hood 3 shown in FIG. 18 is designed so that it forms the right angle or an angle closer to the right angle with respect to the light beam radially incident from the object to the observation portion 6.

In this connection, in order to obtain an excellent observation image in the peripheral visual field range, it is preferable that the diameter-reduced portion 3a which exists in the visual field of the objective optical system 30 has such a spherical shape as to be centered about the observation portion 6 so that the front end hood 3 forms the right angle or an angle closer to the right angle with respect to the light beam radially incident from the object to the observation portion 6.

Figure 19:
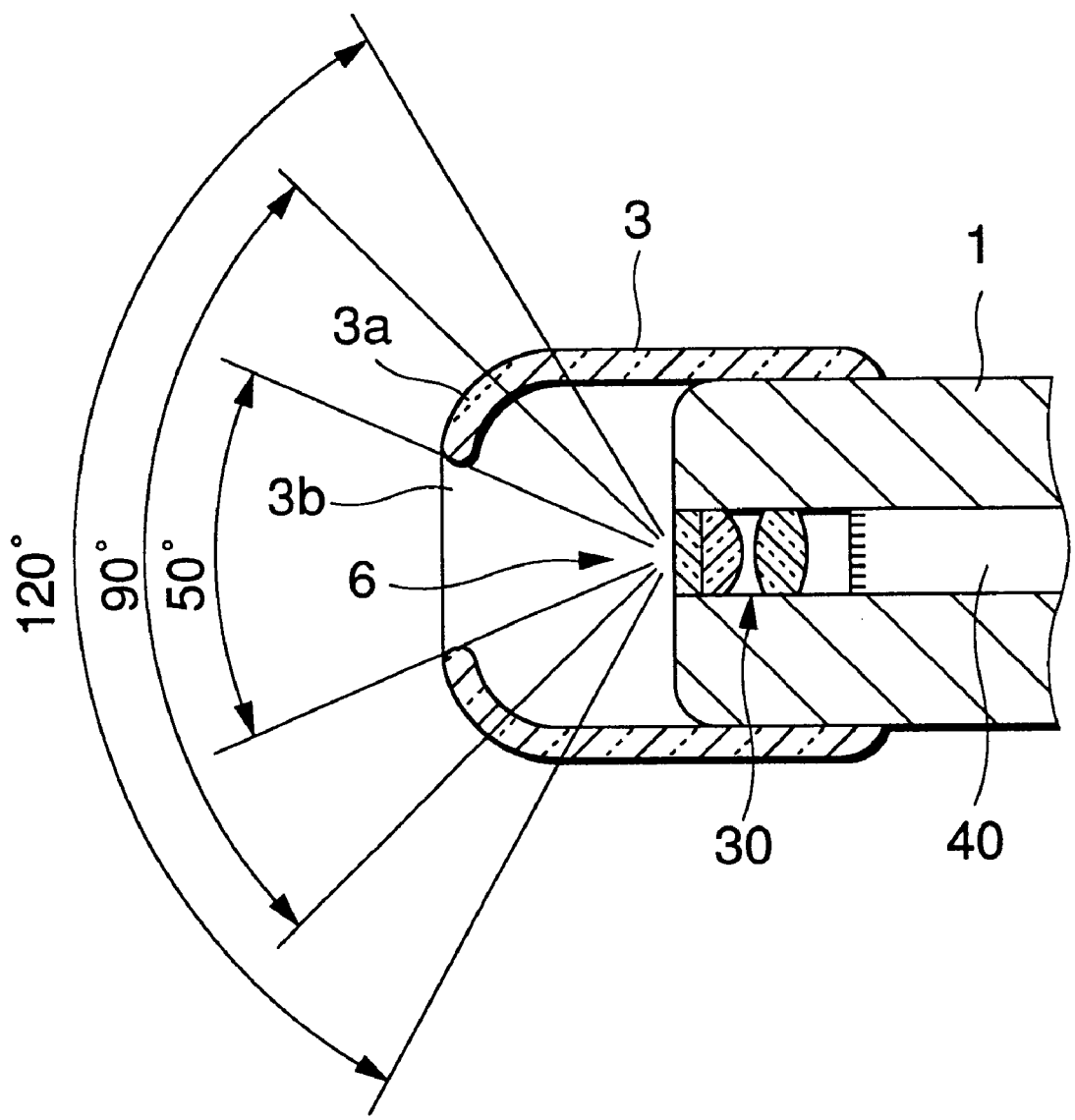
FIG. 19 is a side section view of another front end hood attached to the insertion section front end portion of the endoscope.

FIG. 19 schematically shows further another front end hood 3 made of transparent material, in which no bulged portion is formed, but a diameter-reduced portion 3a in a spherical shape is formed such that the maximum diameter of the spherical diameter-reduced portion is equal to the diameter of the cylindrical shaped portion of the front end hood 3 and it gradually approaches the optical axis. The center area of the spherical diameter-reduced portion 3a is formed as a circular opening 3b. Light beams in the visual field range of 50° or less of the observation range pass through the opening 3b.

The front end hood 3 is attached to the insertion section front end 1 such that the diameter-reduced portion 3a of the front end hood 3 exists from a vicinity of a position where a light beam of the maximum visual field (120°) is transmitted.

Therefore, an excellent observation image which is not transmitted through the transparent wall of the front end hood 3 is obtained in the visual field range of 50° or less, and an excellent observation image which is substantially free from distortion is obtained in the visual field range of 50° to 90° where observation light beams are transmitted through the transparent wall of the front end hood 3 substantially at a right angle.

Also in the visual field range of 90° to 120° which is outside the above-mentioned range, the angle of observation light beams with respect to the front end hood 3 is close to a right angle, and hence an observation image of excellence of a permissible degree is obtained.

Figure 20:
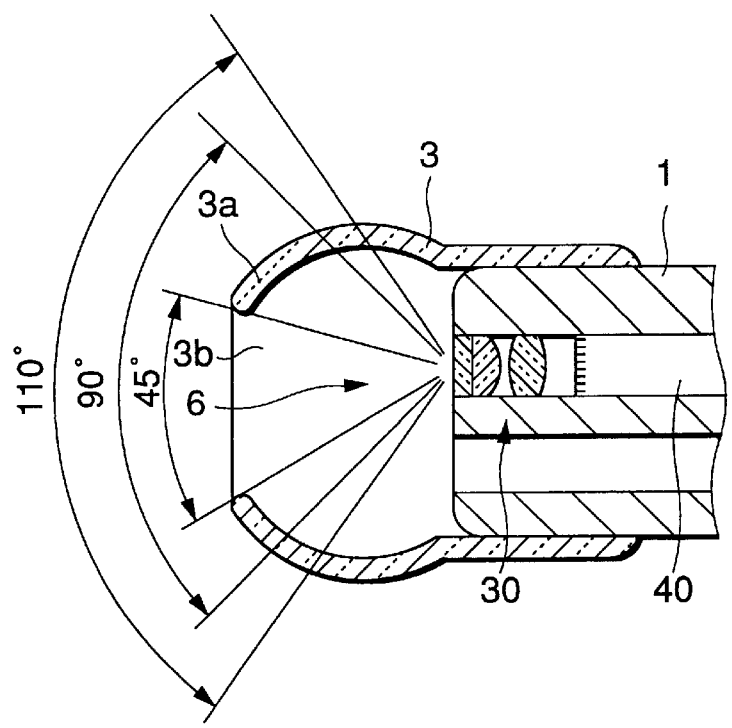
FIG. 20 is a side section view of further another front end hood attached to the insertion section front end portion of the endoscope.

FIG. 20 schematically shows a front end hood 3 which is similar to that shown in FIG. 14 but is different in that the diameter of the front opening end 3b is smaller than the diameter of the insertion section front end 1 of the endoscope. Light beams in the visual field range of 45° or less of the observation range pass through the opening 3b, and therefore, in the visual field range of 45° or less, an observation image which is not transmitted through the front end hood 3 is obtained.

In the visual field range of 45° to 90° where observation light beams are transmitted through the front end hood 3 at an angle close to a right angle, an excellent observation image which is substantially free from distortion is obtained. Also, in the visual field range of 90° to 110° which is outside the above-mentioned range, an observation image of excellence of a permissible degree is obtained.

Figure 21:
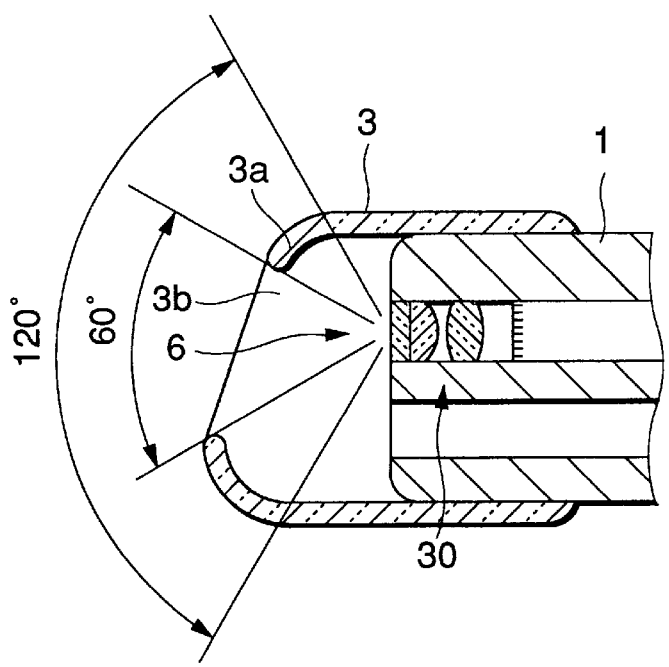
FIG. 21 is a side section view of further another front end hood attached to the insertion section front end portion of the endoscope.

FIG. 21 schematically shows further another front end hood 3, in which a front opening end 3b of the front end hood 3 is inclined so that the projection length of the front end hood 3 on the side (the upper side in this case) which is closer to the optical axis of the objective optical system 30 is made shorter.

The spherical diameter-reduced portion 3b is formed in an inclined manner in consideration of the maximum visual field of the objective optical system 30, and the circular opening 10b at the front end is formed in a visual field range of 60°.

The spherical diameter-reduced portion 3a starts from a position which is closer to the insertion section front end portion 1 than a position where a light beam of the maximum visual field 120° of the observation range is transmitted. Light beams of the visual field angle of 120° is transmitted through the spherical diameter-reduced portion 3a.

An observation image which is not transmitted through the transparent wall of the front end hood 3 is obtained in the visual field range of 60° or less, and an excellent observation image of reduced distortion is obtained in the visual field range of 60° to 120° which is outside the above-mentioned range.

As described above, the diameter-reduced portion 3a of the transparent front end hood 3 makes it possible to obtain the less-distorted, excellent observation image in a periphery of a wide visual field. Further, the spherical shape or the diameter-reduced shape of the front end portion of the front end hood 3 makes it possible to insert the endoscope easily into a body cavity without damaging the mucosa surface.

Figure 22:
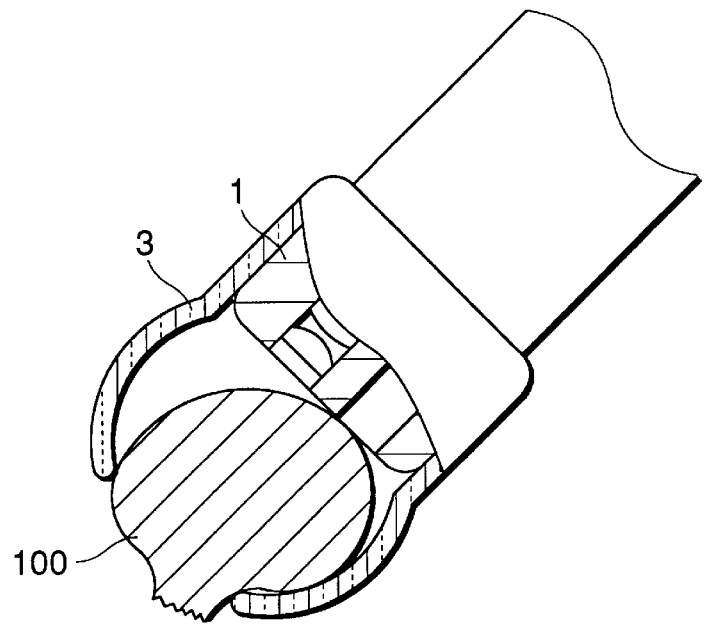
FIG. 22 is a section view showing a state where a polyp is recovered by the endoscope to which the front end hood shown in FIG. 20 is provided.
Figure 22:
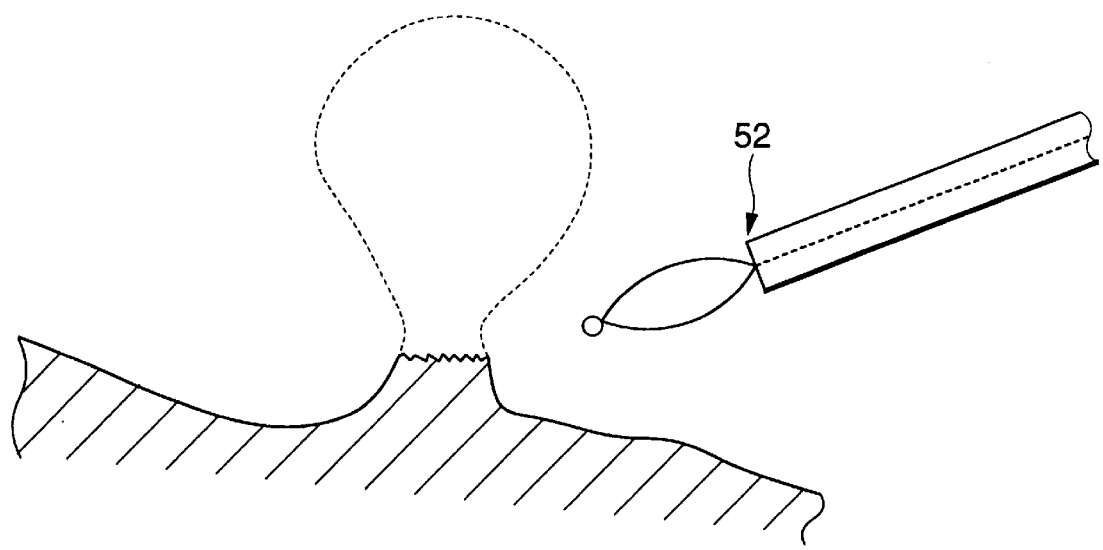
Figure 23:
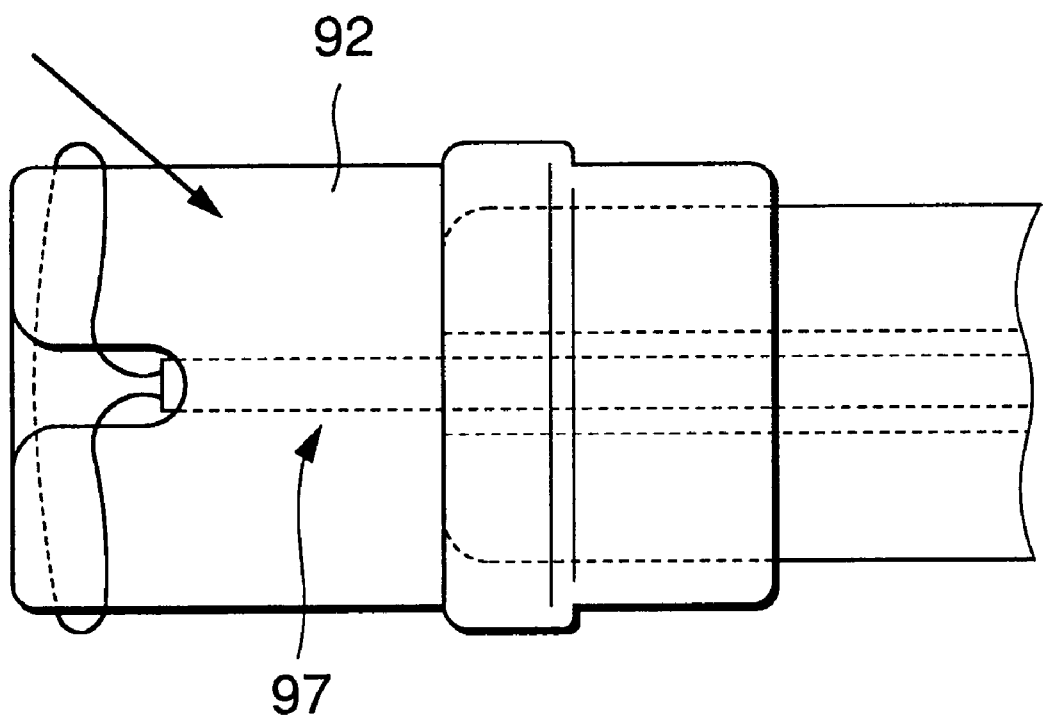
FIG. 23 is a side view of a prior art front end hood for an endoscope.

As shown in FIG. 22, a polyp 100 which has been resected by a high-frequency snare 52 or the like may be sucked to be recovered with being accommodated in the front end hood 10. In such a case, the diameter-reduced shape of the front end of the front end hood 3 prevents even a small polyp 100 from falling off, so as to be surely recovered.

What is claimed is:

1. A hollow front end hood in combination with an endoscope, said endoscope including a source of suction and a suction channel, said front end hood comprising a first end attachable to an insertion section front end portion of said endoscope, and a second end opposite from said first end, said front end hood further comprising a diameter-increased portion between said first and second ends, wherein when said second end is pressed against a surface of a body, a part of the body may be sucked into said front end hood upon actuation of said source of suction.

2. A hollow front end hood according to claim 1, wherein said diameter-increased portion defines a conical inner space enlarged in a direction from said first end to said second end.

3. A hollow front end hood according to claim 2, wherein said first end is smaller in diameter than said second end.

4. A hollow, transparent front end hood comprising a first end attachable to and extending from an insertion section front end portion of an endoscope having a field of view, and a second end opposite from said first end, said front end hood further comprising a diameter-decreased portion between said first and second ends, wherein light beams in said field of view are transmitted at substantially right angles through said diameter-decreased portion of said front end hood.

5. A hollow front end hood according to claim 4, further comprising:

a diameter-increased portion located between said diameter-decreased portion and said first end.

6. A hollow front end hood according to claim 5, wherein both of said diameter-increased and decreased portions are spherical.

7. A hollow front end hood according to claim 6, wherein said first end is substantially equal in diameter to said second end.

8. A hollow front end hood according to claim 4, wherein said first end is larger in diameter than said second end.

9. A hollow front end hood according to claim 4, wherein said diameter-decreased portion is spherical.

10. A hollow front end hood according to claim 4, wherein said diameter-decreased portion has a maximum diameter substantially equal to a diameter of said first end, and a minimal diameter substantially equal to a diameter of said second end.

11. A hollow front end hood according to claim 4, wherein said second end is inclined with respect to said first end.

12. A hollow front end hood according to claim 1, wherein said hollow front end hood is transparent.

13. An endoscope comprising:

an insertion section having a front end;

an observation port disposed in said front end;

a front end hood formed from optically transparent material, said front end hood having a first end and a second end, said first end being attached to said front end of said insertion section so that said second end of said hood is spaced from said front end of said insertion section and that said observation port is positioned inside said front end hood, wherein a third portion of said front end hood closer to said second end of said hood than to said first end thereof is formed into a spherical shape constricted in a direction from said first end of said hood to said second end thereof, wherein light beams received by said observation port are transmitted at substantially right angles through the optically transparent material of said third portion of said front end hood.

14. An endoscope according to claim 13, wherein, said front end hood has a uniform thickness at least in said spherical, third portion.

15. An endoscope according to claim 13, wherein said front end hood is detachable with respect to said front end of said insertion section.

16. An endoscope according to claim 13, wherein a fourth portion of said front end hood between said first end and said third portion is formed into a cylindrical shape, and said spherical, third portion has a maximum diameter equal to a diameter of said cylindrical, fourth portion.

17. An endoscope according to claim 13, wherein a fourth portion of said front end hood between said first end and third portion is formed into a cylindrical shape, and said spherical, third portion has a maximum diameter larger than an outer diameter of said cylindrical, fourth portion.

18. An endoscope according to claim 16, wherein said second end of said front end hood is inclined with respect to an axis of said cylindrical, fourth portion.

19. An endoscope comprising:

an insertion section having a front end;

an observation port disposed in said front end;

an optically transparent front end hood having a first end and a second end, said first end being attached to said front end of said insertion section so that said second end of said hood is spaced from said front end of said insertion section and that said observation port is positioned inside said front end hood, wherein a third portion of said front end hood closer to said second end of said hood than to said first end thereof is formed into a spherical shape constricted in a direction from said first end of said hood to said second end thereof, and wherein a fourth portion of said front end hood between said first end and said third portion is formed into a cylindrical shape, and said spherical, third portion has a maximum diameter at least equal to a diameter of said cylindrical, fourth portion.

20. An endoscope according to claim 19, wherein said spherical, third portion has a maximum diameter equal to a diameter of said cylindrical, fourth portion.

21. An endoscope according to claim 19, wherein said spherical, third portion has a maximum diameter larger than an outer diameter of said cylindrical, fourth portion.

22. An endoscope according to claim 19, wherein said second end of said front end hood is inclined with respect to an axis of said cylindrical, fourth portion.

* * * * *